US012357159B2

(12) United States Patent
Eastwood (10) Patent No.: US 12,357,159 B2
(45) Date of Patent: Jul. 15, 2025

(54) SURGICAL SCOPE WITH REMOVABLE LUMEN

(71) Applicant: The Government of the United States, as represented by The Director of the Defense Health Agency, Fort Detrick, MD (US)

(72) Inventor: Matthew Alan Eastwood, Travis AFB, CA (US)

(73) Assignee: The Government of The United States, as Represented by The Director of the Defense Health Agency, Ft. Detrick, MD (US)

( * ) Notice: Subject to any disclaimer, the term of this patent is extended or adjusted under 35 U.S.C. 154(b) by 427 days.

(21) Appl. No.: 16/585,618

(22) Filed: Sep. 27, 2019

(65) Prior Publication Data

US 2021/0093160 A1 Apr. 1, 2021

(51) Int. Cl.
*A61B 1/005* (2006.01)
*A61B 1/00* (2006.01)
(Continued)

(52) U.S. Cl.
CPC ........ *A61B 1/0055* (2013.01); *A61B 1/00137* (2013.01); *A61B 2017/0023* (2013.01); *C08G 73/10* (2013.01); *C08L 33/12* (2013.01)

(58) Field of Classification Search
CPC .............. A61B 1/00137; A61B 1/0055; A61B 1/00101; A61B 1/00066; A61B 1/015; A61B 1/00006; A61B 1/018; A61B 17/00234; A61B 17/702; A61B 17/7019; A61B 17/7002; A61B 17/7001;
(Continued)

(56) References Cited

U.S. PATENT DOCUMENTS 4,175,545 A * 11/1979 Termanini .......... A61B 1/00091
600/479
4,741,326 A * 5/1988 Sidall ................. A61B 1/00142
600/125
(Continued)

FOREIGN PATENT DOCUMENTS

CN 204293111 U 4/2015
CN 204708808 U 10/2015
(Continued)

OTHER PUBLICATIONS

Google Patent Machine Translation of CN204293111U, 4 pages total.
(Continued)

*Primary Examiner* — Anh Tuan T Nguyen
*Assistant Examiner* — Megan Elizabeth Monahan
(74) *Attorney, Agent, or Firm* — Banner & Witcoff, Ltd.

(57) ABSTRACT

A disposable insert for an endoscope. The disposable insert includes a flexible shaft and a cap. The flexible shaft has a distal end, a proximal end, and a lumen extending therebetween and is configured to be inserted into a lumen of an endoscope. The cap is operably coupled to the distal end of the flexible shaft and is configured to form a fluid-tight seal and secure the flexible shaft to a distal end of the endoscope. The cap also has a lumen extending therethrough that is coaxial to the lumen of the flexible shaft.

23 Claims, 11 Drawing Sheets

(51) Int. Cl.
*A61B 17/00* (2006.01)
*C08G 73/10* (2006.01)
*C08L 33/12* (2006.01)

(58) Field of Classification Search
CPC ........ A61B 5/15142; A61B 2017/0023; A61B 2017/00269; A61B 2017/0034; A61B 17/7032; A61B 17/7007; A61B 17/7091
See application file for complete search history.

(56) References Cited

U.S. PATENT DOCUMENTS

| | | | |
|---|---|---|---|
| 4,794,911 A * | 1/1989 | Okada | A61B 1/00165 600/127 |
| 4,852,551 A | 8/1989 | Opie et al. | |
| 5,257,773 A | 11/1993 | Yoshimoto et al. | |
| 5,630,782 A | 5/1997 | Adair | |
| 5,735,792 A | 4/1998 | Hoaek | |
| 5,938,586 A | 8/1999 | Wilk et al. | |
| RE37,772 E | 6/2002 | Kelleher | |
| 6,464,632 B1 | 10/2002 | Taylor | |
| 6,503,196 B1 | 1/2003 | Kehr et al. | |
| 6,827,683 B2 | 12/2004 | Otawara | |
| 6,908,428 B2 | 6/2005 | Aizenfeld et al. | |
| 8,398,540 B2 | 3/2013 | Hassidov et al. | |
| 8,485,966 B2 | 7/2013 | Robertson | |
| 8,979,738 B2 | 3/2015 | Hsu et al. | |
| 9,204,785 B2 | 12/2015 | Wagner et al. | |
| 9,498,108 B1 | 11/2016 | Lombardi | |
| 2003/0088259 A1 * | 5/2003 | Staid | F16L 17/035 606/1 |
| 2005/0256373 A1 | 11/2005 | Bar-Or et al. | |
| 2006/0111612 A1 * | 5/2006 | Matsumoto | A61B 1/0011 600/129 |
| 2006/0149131 A1 | 7/2006 | Or | |
| 2007/0112337 A1 | 5/2007 | Salman et al. | |
| 2007/0270646 A1 | 11/2007 | Weiner | |
| 2008/0172042 A1 | 7/2008 | House | |
| 2008/0249362 A1 | 10/2008 | Jiang et al. | |
| 2014/0058200 A1 | 2/2014 | Nimkar et al. | |
| 2016/0120395 A1 | 5/2016 | Qi | |
| 2018/0084971 A1 | 3/2018 | Truckai et al. | |

FOREIGN PATENT DOCUMENTS

| | | |
|---|---|---|
| WO | 1994027511 | 12/1994 |
| WO | 1995006429 A1 | 3/1995 |

OTHER PUBLICATIONS

Google Patent Machine Translation of CN204708808U, 4 pages total.

* cited by examiner

SURGICAL SCOPE WITH REMOVABLE LUMEN

RIGHTS OF THE GOVERNMENT

The invention described herein may be manufactured and used by or for the Government of the United States for all government purposes without the payment of any royalty.

FIELD OF THE INVENTION

The invention described herein generally relate to medical devices and, more particularly, to flexible endoscopes.

BACKGROUND OF THE INVENTION

Endoscopes are medical devices that allow healthcare practitioners to inspect the inside of a patient's body without requiring incisions. For example, endoscopy procedures may including the insertion of an endoscope through the mouth of a patient, down the esophagus, and into the stomach and/or small intestine. While reusing endoscopes is more cost effective than using new endoscopes for each new patient there has recently been news of a high incidence of transmission of infections due to improper or incomplete sterilization of reusable, flexible endoscopes between patients. Although the reusable endoscopes typically undergo high-level disinfection processes after manual cleaning, bacteria often forms a biofilm on walls of the multiple channels associated with these devices, enabling the bacterial to adhere to and remain on the walls of these channels. The presence of biofilm, thus, increases the risk of infection to subsequent patients and, possibly, the healthcare practitioners using the endoscopes.

Further cleaning or enhanced cleaning of an endoscope is generally not a viable approach to reducing the chances of infection since the current cleaning techniques are often incapable of removing all biofilm from the endoscope. Moreover, some microbes and bacteria associated with anatomy exposed during endoscopies may be resistant to certain detergents or antimicrobial cleaners.

Thus, there remains a need to devices and methods that better utilize reusable endoscopes while minimizing cross-contamination risks.

SUMMARY OF THE INVENTION

The present invention overcomes the foregoing problems and other shortcomings, drawbacks, and challenges of conventional, reusable endoscopes. While the invention will be described in connection with certain embodiments, it will be understood that the invention is not limited to these embodiments. To the contrary, this invention includes all alternatives, modifications, and equivalents as may be included within the spirit and scope of the present invention.

A disposable insert for an endoscope. The disposable insert includes a flexible shaft and a cap. The flexible shaft has a distal end, a proximal end, and a lumen extending therebetween and is configured to be inserted into a lumen of an endoscope. The cap is operably coupled to the distal end of the flexible shaft and is configured to form a fluid-tight seal and secure the flexible shaft to a distal end of the endoscope. The cap also has a lumen extending therethrough that is coaxial to the lumen of the flexible shaft.

The endoscope may be a conventional endoscope having light fibers, camera fibers, steering mechanisms, or combinations thereof.

Another embodiment of the present invention is directed to an endoscopic system comprising an endoscope and a disposable insert. The endoscope includes a first flexible shaft having a first proximal end, a first distal end, and a first lumen extending therebetween. A hub is coupled to the first proximal end of the first flexible shaft, and a controller, positioned within the hub, is configured to control at least one operation, the at least one operation selected from suction, irrigation, lighting, imaging, mechanical manipulation, and electrical manipulation. The disposable insert includes a second flexible shaft having a second proximal end, a second distal end, and a second lumen extending therebetween. A cap is coupled to the distal end of the second flexible shaft and is configured to form a fluid-tight seal and secure the flexible shaft to a distal end of the endoscope. The cap also has a lumen that is coaxial to the lumen of the flexible shaft. The second proximal end of the second flexible shaft is operably coupled to the controller such that the at least one operation is performed through the second lumen of the second flexible shaft.

Another embodiment herein provides an endoscope system comprising an endoscope having a flexible shaft having a first distal end, a first proximal end, and a first lumen extending therebetween. A disposable insert has a second distal end, a second proximal end, and a second lumen extending therebetween. The disposable insert is configured to be received by the first lumen of the flexible shaft and move in sliding relation thereto. A cap configured to operably secure the disposable insert to the flexible shaft of the endoscope. The cap may be constructed from an optically transparent material.

Some aspects of the invention may include a disposable controller operatively connected to the disposable insert that is configured to control suction and irrigation through the disposable insert. The endoscope system may include a housing attached to the first distal end of the flexible shaft of the endoscope. The housing includes a cavity and a cover. The disposable controller is disposed within the cavity and under the cover. The cover may include at least one hole configured such that at least one button of the controller to extend therethrough.

The flexible shaft of the endoscope may engage the disposable insert via a threaded connection.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 1:
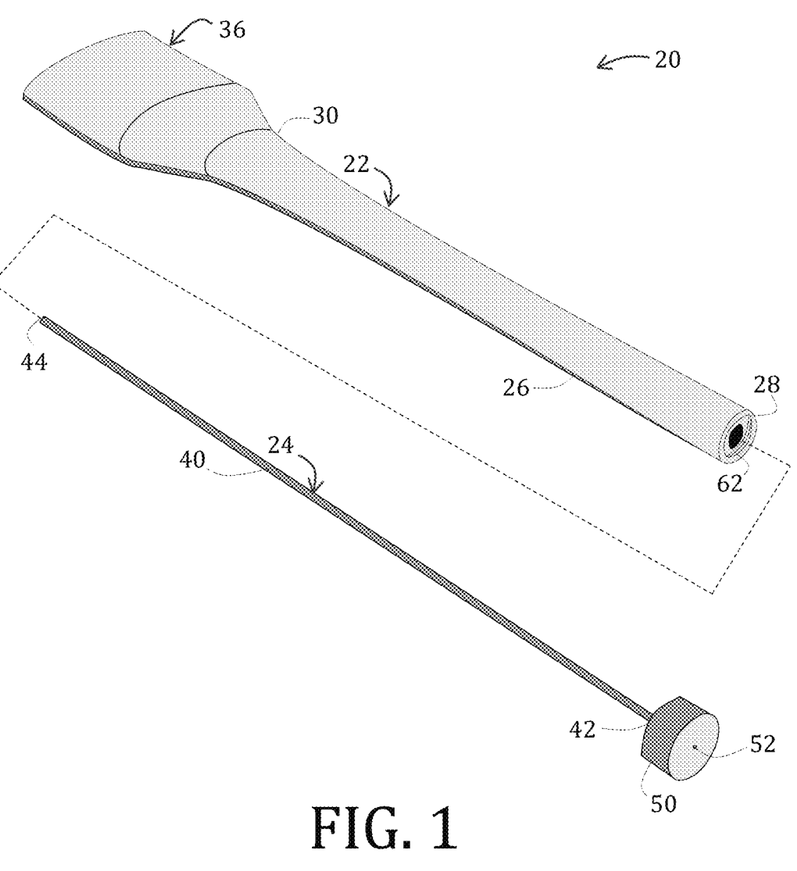
FIG. 1 is an exploded, perspective view of an endoscopic system comprising an endoscope and a disposable insert according to an embodiment of the present invention.
Figure 2:
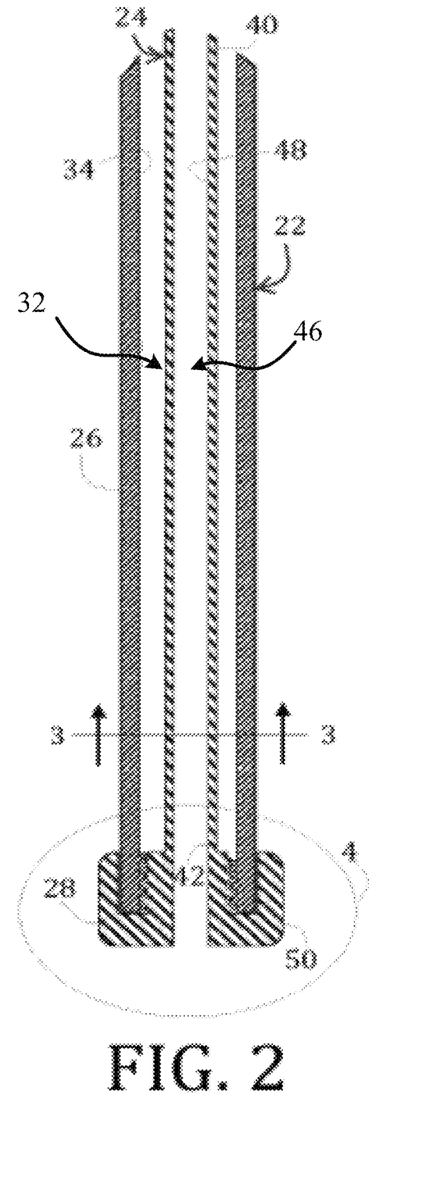
FIG. 2 is a length-wise, cross-sectional view of the endoscope and disposable insert of FIG. 1.
Figure 3:
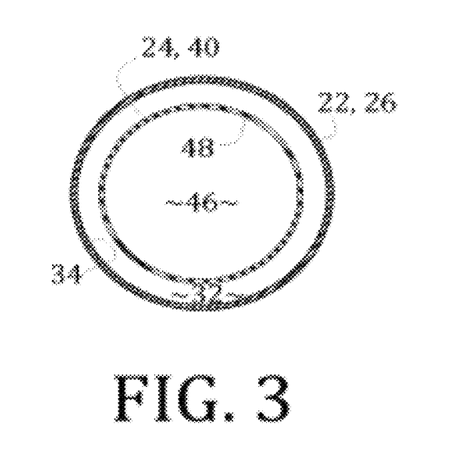
FIG. 3 is a cross-sectional view taken along the line 3-3 in FIG. 2.

Referring now to the figures, and more particularly to FIGS. 1 and 2, an endoscopic system 20 having an endoscope 22 and a disposable insert 24 according to a first embodiment of the present invention is shown. The endoscope 22 includes a flexible shaft 26 having a distal end 28, a proximal end 30, and a lumen 32 extending therebetween defined by an inner wall 34. The flexible shaft 26 may be configured to be any suitable length, outer wall thickness, and may comprise silicon, plastic, or other durable and, preferably, hypoallergenic material that has a decreased risk for tissue reactions or allergies when contacting a person. The lumen 32 may be configured to be any suitable length and diameter corresponding to an inner diameter of the flexible shaft 26 and is generally configured to have the same length as the flexible shaft 15.

The endoscope 22 further comprises a hub 36 operably coupled to the proximal end 30 of the flexible shaft 26. The hub 36 may be bonded or sealed to the proximal end 30 or may be a continuous, unitary structure with the flexible shaft 26, according to some examples. The hub 36 may comprise any suitable size or configuration and may comprise silicon, plastic, or any other durable material that does not have the potential for tissue reactions or risk of allergies when contacting a person. In an example, the hub 36 may comprise the same material as the flexible shaft 26. Furthermore, the hub 36 may comprise at least one component is configured to accommodate a controller 38 (FIG. 6) such that the controller 38 (FIG. 6) is substantially contained within the hub 36.

The disposable insert 24 of the endoscopic system 20 includes a flexible shaft 40 wall having a distal end 42, a proximal end 44, and a lumen 46 extending therebetween defined by an inner wall 48. The lumen 46 may be configured to permit passage and suction of biofluids, tissues, or any other objects from a patient.

According to some examples, the disposable insert 24 may be any length and thickness and may comprise silicon, plastic, or any other durable and, preferably, hypoallergenic material that has a decreased risk for tissue reactions or allergies when contacting a person.

Generally, an outer diameter of the flexible shaft 40 of the disposable insert 24 should be shaped and sized so as to be inserted into the lumen 32 of the flexible shaft 26 of the endoscope 22 and to move in sliding relation thereto. That is, an inner diameter of the flexible shaft 26 (i.e., a diameter of the lumen 32) should be greater than the outer diameter of flexible shaft 40 the disposable insert 24. If desired, and according to some embodiments, the inner wall 24 of the flexible shaft 26 of the endoscope 22, an outer surface of the flexible shaft 40 of the disposable insert 24, or both may be coated with a biologically safe lubricant to facilitate, enhance, or enable slidable movement between the endoscope 22 and the disposable insert 24.

Although not shown, the disposable insert 24 may be configured as a bifurcated tube (e.g., sectioned along a length-wise axis, for example, or another axis parallel to the length-wise axis), such that the disposable insert 24 may comprise a plurality of lumens.

The distal end 42 of the disposable insert 24 further comprises a cap 50 operably coupled thereto and configured to operably secure the distal end 42 of the disposable insert 24 relative to the distal end 28 of the endoscope 22. The cap further includes a lumen 52 that may be coaxial and coextensive with the lumen 46 of the disposable insert 24. The cap 50 may vary in length and thickness and may comprise silicon, plastic, or any other durable material, which does not have the potential for tissue reactions or risk of allergies when contacting a person.

Figure 4:
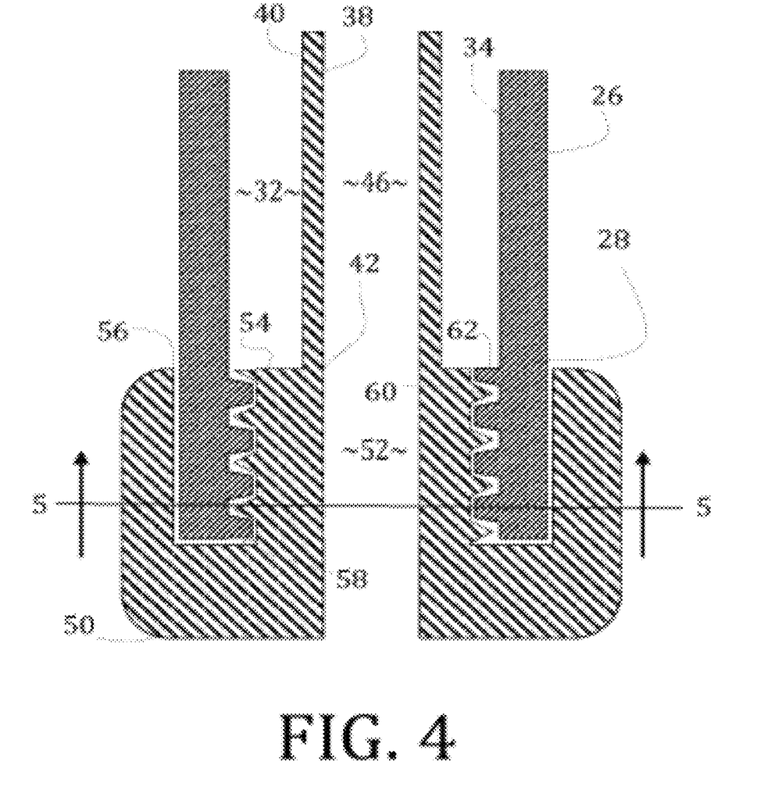
FIG. 4 is an enlarged, cross-sectional view taken from the enclosed portion in FIG. 2.
Figure 4A:
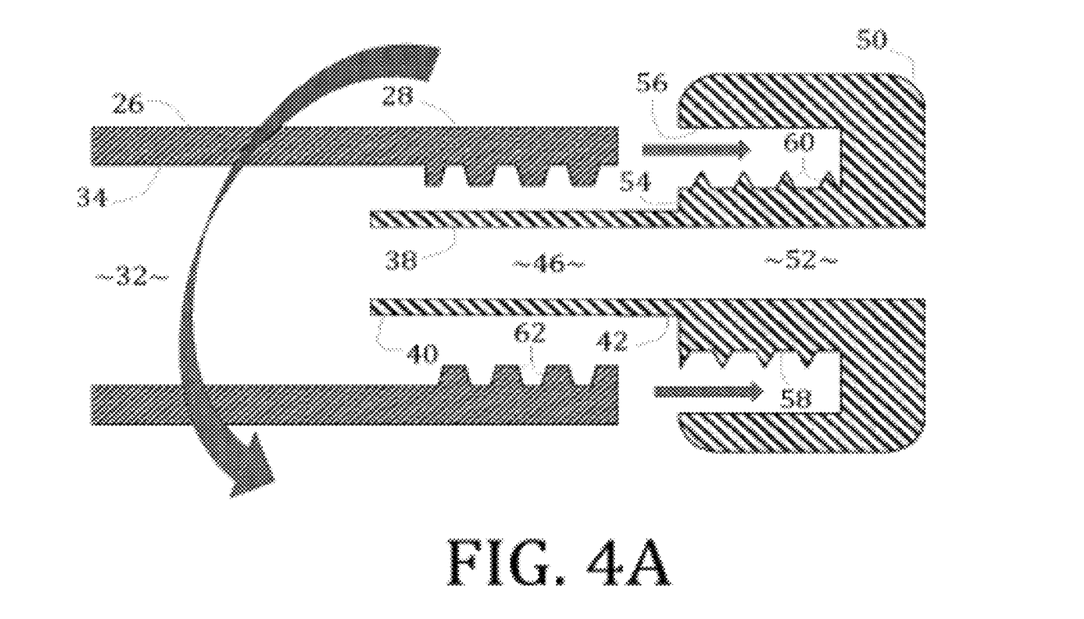
FIG. 4A is an exploded view of FIG. 4.
Figure 5:
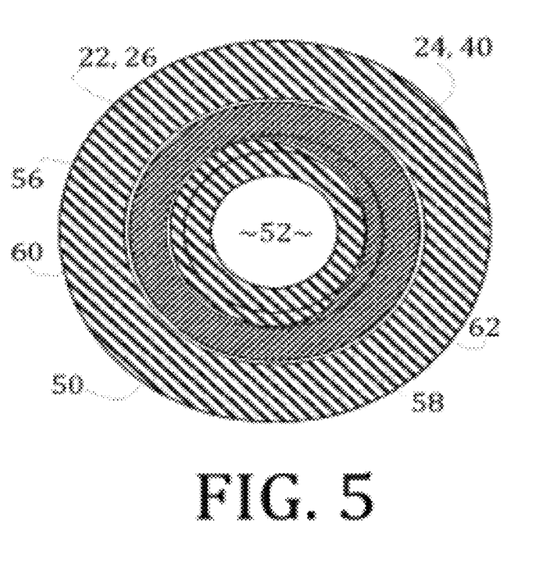
FIG. 5 is a cross-sectional view taken along the line 5-5 in FIG. 4.

With reference now to FIGS. 2, 4, and 5, additional details of the cap 50 are described. The cap 50 may be substantially cylindrical in cross-section and have a length that is shorter than a length of either flexible shaft 26, 40. According to one embodiment, a proximal surface 54 of the cap 50 may include a recess 56 that is configured to receive the distal end 28 of the endoscope 22, which is more particularly illustrated in FIG. 4A. In the particular, illustrative embodiment of FIGS. 4 and 4A, a medial wall 58 of the recess 56 includes threads 60 that are configured to receive corresponding threads 62 on the inner wall 34 at the distal end 28 of the flexible shaft 26 of the endoscope 22. The threads 60, 62 may engage through a conventional male/female threaded engagement; however, alternative engagement mechanisms may be used, such as press or friction fit, use of screws or bolts, or other retaining mechanism. The cap 50 may be, at least partially, constructed from silicon, plastic, or any other durable material, which does not have the potential for tissue reactions or risk of allergies when contacting a person.

The threaded engagement should not be restricted to the particular illustrated configuration. Moreover, the shape, size, number, and length of the threaded engagement may be configured in various ways that would be understood by the skilled artisan having the benefit of the disclosure made herein.

While not specifically illustrated herein, a gasket may be positioned within the recess 56 of the cap 50 and may be configured to form a seal between the cap 50 of the disposable insert 24 and the flexible shaft 26 of the endoscope 22. According to some embodiments of the present invention, the gasket may be configured as an O-ring gasket or any other suitable configuration or shape constructed of rubber, silicon, or any other suitable material that provides sealing capacity and that does not have the potential for tissue reactions or risk of allergies when contacting a person. For one exemplary embodiment, the gasket may extend over the distal end 28 of the flexible shaft 26.

According to the embodiment illustrated in FIGS. 1-5, the disposable insert 24 may be exposed to biofluids and tissues during a procedure and then removed from the flexible shaft 26 of the endoscope 22 and disposed in an appropriate manner. The disposable insert 24 may, therefore, be a single use device that is discarded without undergoing cleaning or subsequent reuse. The endoscope 22, with limited exposure to biomaterials, may be cleaned and reused. Moreover, because the endoscope 22 is not exposed to biomaterials, the endoscope 22 is not susceptible to biofilm growth. Conventional cleaning disinfection and cleaning may then be used with greater success and reducing risk of infection to a subsequent patient.

Figure 6:
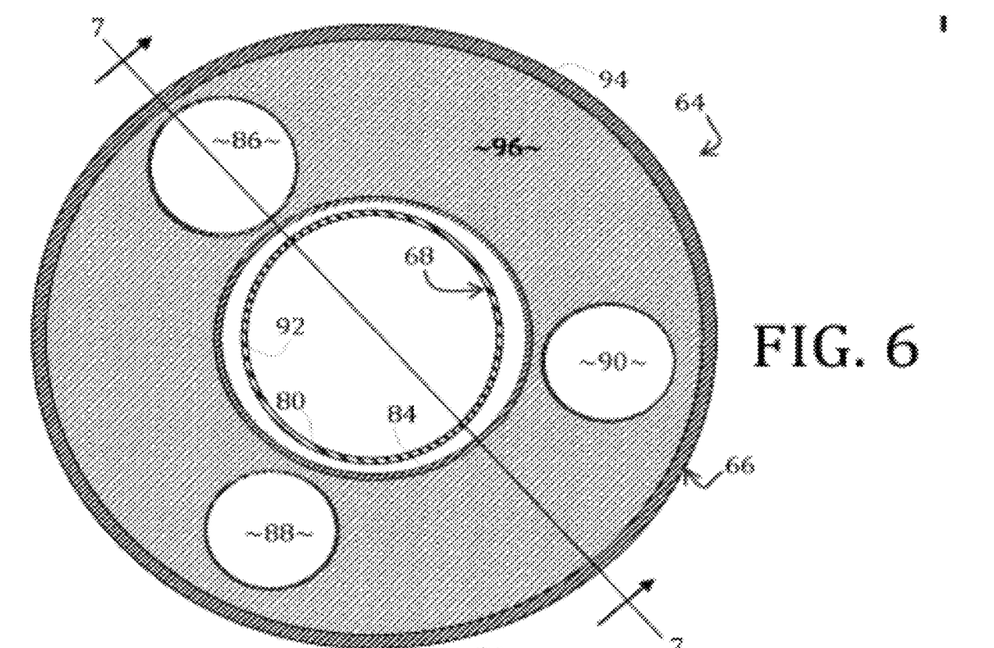
FIG. 6 is a cross-sectional view of a cap of the disposable insert according to another embodiment of the present invention.
Figure 7:
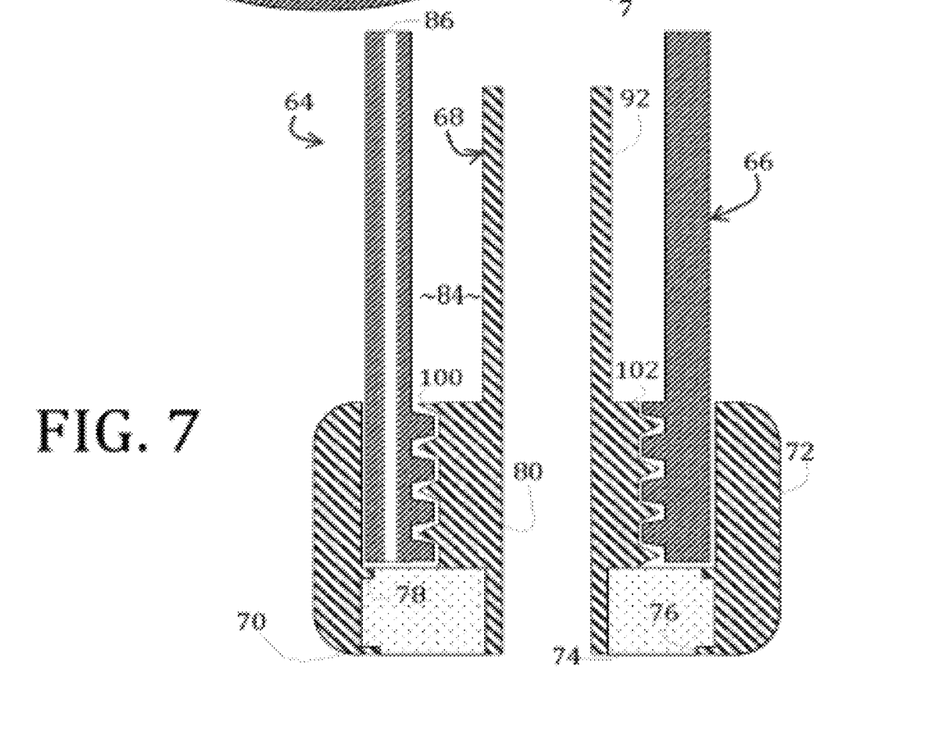
FIG. 7 is a cross-sectional view taken along the line 7-7 in FIG. 6.

Referring now to FIGS. 6 and 7, an endoscopic system 64 according to another embodiment of the present invention is shown. The endoscopic system 64 includes an endoscope 66 that is similar to the endoscope 22 of FIG. 1; however, the endoscopic system 64 further comprises a disposable insert 68 having a optically transparent distal end 70. In particular the distal end 70 of the disposable insert 68 includes a molded body 72 and an optically transparent window 74 secured therein. The transparent window 74 may comprise any suitable configuration, size, or shape including a disk shape and may be constructed from acrylic, glass, poly (methyl methacrylate) (PMMA), polyimide, plastic material, sapphire, polycarbonates, polymers, zinc-selenide, etc. The transparent window 74 may be bonded to the molded body 72 using adhesives or other connecting materials to form a continuous structure. The transparent window 74 may be operatively or constructively connected to the molded body 72 with intervening components (such as distal and proximal lips 76, 78) or friction fit, for example.

The transparent window 74 may have a diameter, as illustrated, that is similar to an outer diameter of the endoscope 66. Generally, the diameter of the transparent window 74 is greater than a diameter of a lumen (defined by inner wall 80) of the disposable insert 68 and less than an outer diameter (defined by an outer wall 82) of the molded body 72.

Use of the particular endoscopic system 64 of FIG. 6 may be of benefit for use with the endoscope 66 includes multiple lumens 84, 86, 88, 90. For instance, a first lumen 84 may be configured to receive a shaft 92 of the disposable insert 68; a second lumen 86 may be configured to receive optics or illumination systems, for example, and to permit movement therethrough; third and fourth lumens 88, 90 may be configured to receive other auxiliary devices and tools, and to permit movement therethrough and in accordance with surgical needs or requirements (for example, imaging equipment). As to the instant embodiment, an illumination system (not shown) may extend through the second lumen 86 such that its emitted light may transmit through the transparent window 74 and illuminate a surgical site. Another exemplary use of the third lumen 88 may include the use of a catheter camera system (not shown) that is configured to permit visualization of the surgical site through the transparent window 74. Of particular note is the fact that the second, third, and fourth lumens 86, 88, 90 are closed off from biocontamination exposure, which is limited to the lumen (defined by the inner wall 80) of the shaft 92 of the disposable insert 68. Such use facilitates sterilization of the illumination system and the catheter camera system.

It would be readily understood by the skilled artisan having the benefit of the disclosure made herein that other arrangements of the lumens 84, 86, 88, 90 are possible, including lumens in an outer wall 94 of the endoscope 66, for example, as opposed to the wall thickness 96 as shown in FIG. 6.

Coupling the molded body 72 to the endoscope 66 may include a threaded engagement 100, 102; however, other mechanisms may also be used. In fact, for embodiments in which the lumens of a multi-lumen endoscope are offset, making a threaded engagement impractical.

Figure 8:
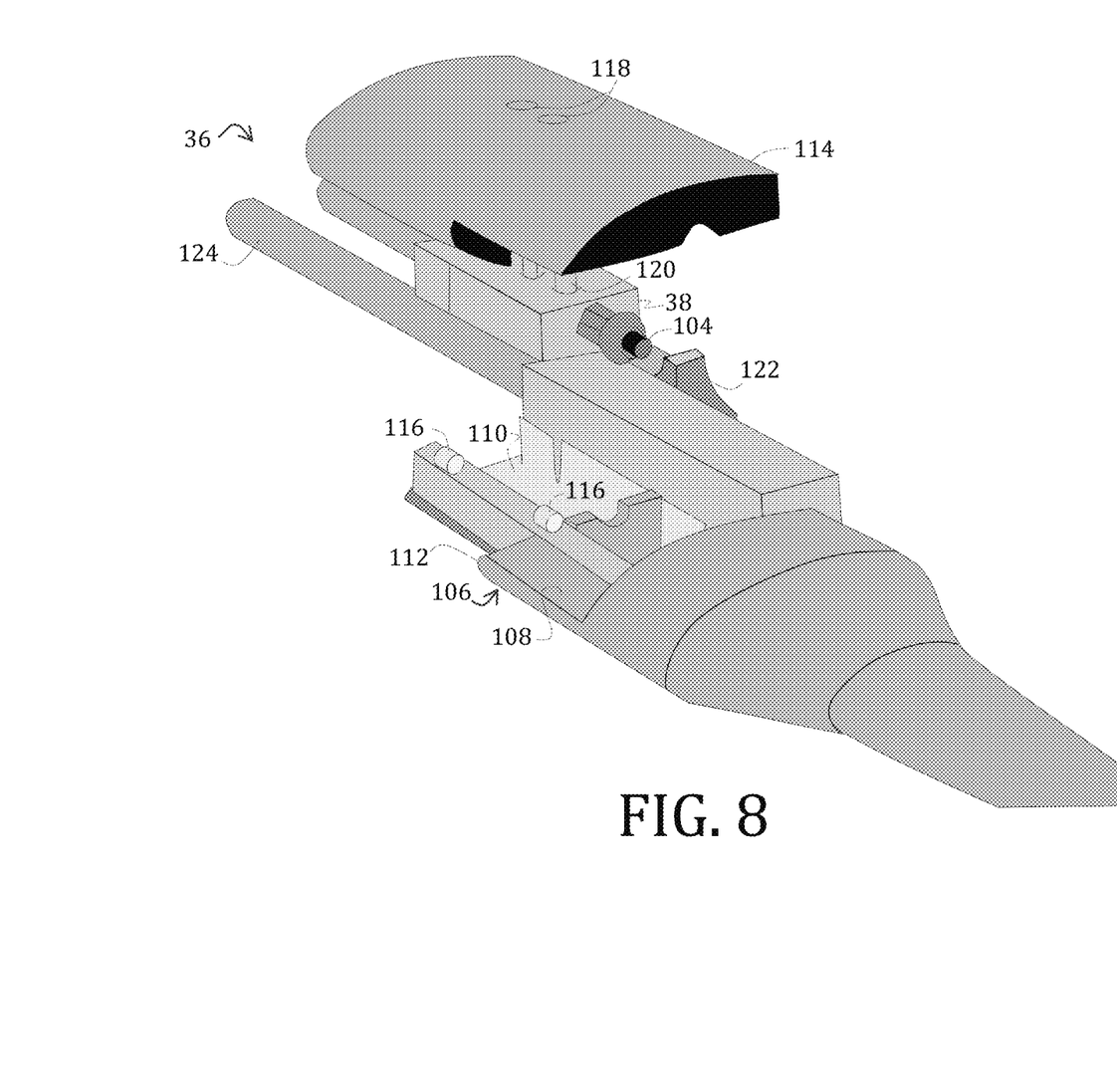
FIGS. 8 and 9 are exploded, side elevational views of a hub of the endoscope of FIG. 1.
Figure 9:
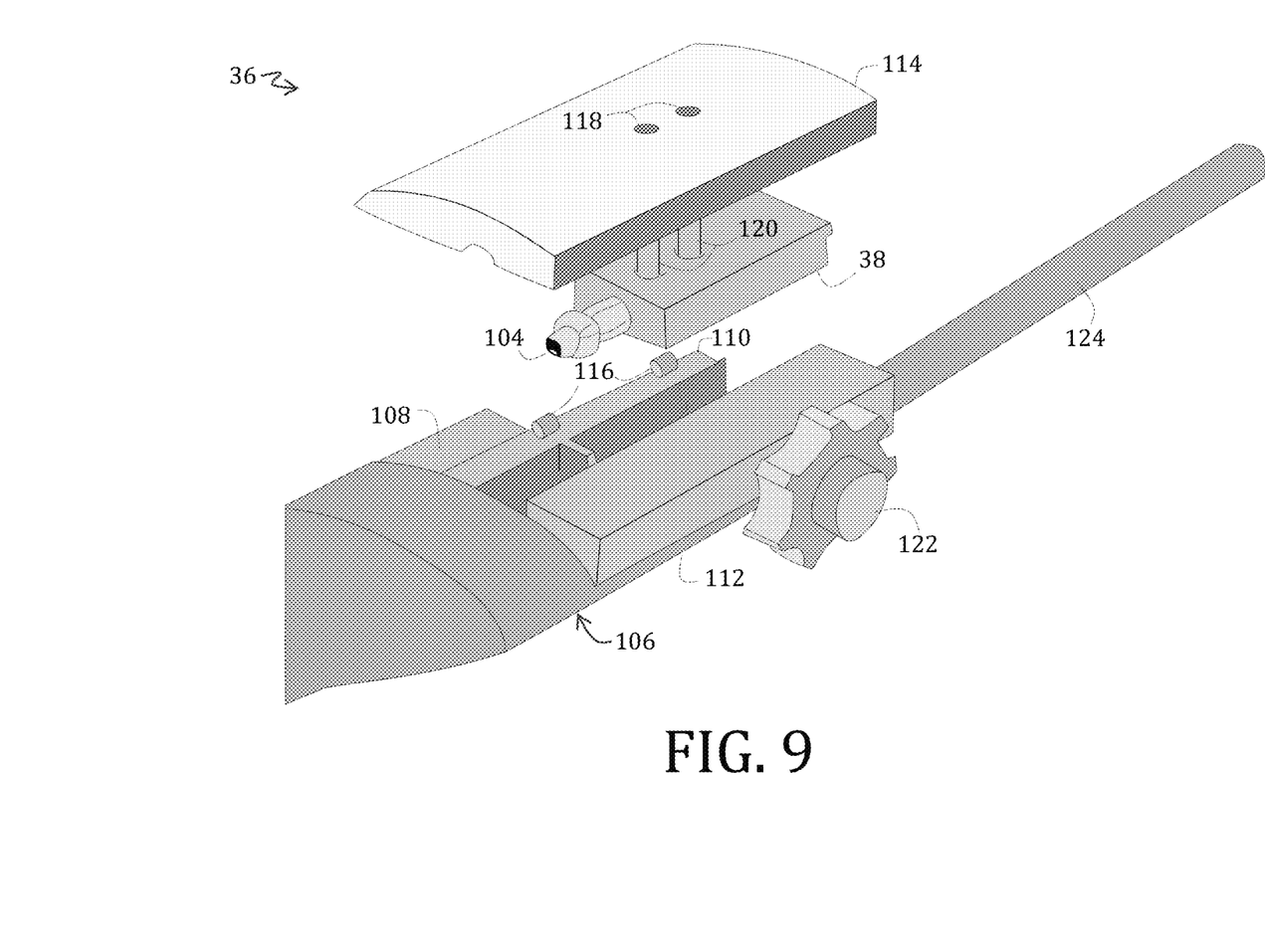

FIGS. 8 and 9 further illustrate details of the hub 36 of the endoscopic system 20. As was noted above, the hub 36 may include a housing 106 configured to enclose a controller 38 therein. The controller 38 may be configured to control various operations and manipulations of the endoscopic system 20 such as suction, irrigation, lighting, imaging, mechanical manipulation, electrical manipulation, and so forth. The controller 38 may be mechanical, electrical, magnetic controller, optical, or a combination thereof. The controller 38 may comprise any suitable mechanisms to allow for the control functionalities described herein. In an example, the controller 38 may comprise a directional controller or steering capabilities.

The controller 38 may include a port 104 configured to operatively receive the proximal end 44 of the shaft 40 of the disposable insert 24. The controller 38, by way of the port 104, is adapted to control suction, irrigation, or both through the disposable insert 24. The controller 38 may be pre-programmed to provide a plurality of levels of suction, irrigation or both. Alternatively, the controller 38 may be operated "on the fly," in real-time, during a procedure. In this way, suction and irrigation are performed through the disposable insert 24 so that removal of biofluids, tissues, or other objects occurs only through the disposable insert 24 without contaminating the endoscope 22.

The controller 38 may be further operatively connected through any of a wired and wireless connection to a computer (not shown), communication device (not shown), display device (not shown), or other device or system (not shown) to allow a user, such as a healthcare practitioner, to view, analyze, and/or process the images/video acquired by way of the endoscopic system 20.

According to some embodiments of the present invention, the controller 38 may be disposable. In this way, and after each procedure, the controller 38 and the disposable insert 24 may both be discarded as opposed to undergoing a cleaning process and be reuse.

The housing 106 for the hub may be operably coupled to the proximal end 30 of the flexible shaft 26 of the endoscope 22, such as by bonding, sealing, adhesive, and so forth. According to some embodiments, the housing 106 and the shaft 26 of the endoscope 22 may comprise a unitary structure. The housing 106 may be any suitable size or configuration and may be constructed from silicon, plastic, etc., or other like, durable material that would not present risk for tissue reactions or allergies when contacting a person.

An internal cavity 108 of the housing 106 may be a single compartment or may be separated into multiple compartments. According to one embodiment, the housing 106 may be configured to accommodate the controller 38 within a first compartment 110 and such that the controller 38 is substantially contained within the housing 106. Alternatively, at least a portion of the controller 38 may extend beyond the housing 106, although this is not specifically illustrated.

The housing 106 may be a singular structure or, as illustrate, a multi-part structure having a base 112 and a cover 114. In some examples, the cover 114 may be snap fit, press fit, or rotatably fit (i.e., through hinged connections 116, as shown) to the base 112. Other connection techniques may be utilized in accordance with the embodiments herein.

As is also illustrated, the cover 114 may include at least one port 118 configured to provide access to a button 120 or switch (not shown) of the controller 38. The button 120 may be directly coupled, or operably coupled, to the controller 38 or may be a separately configured mechanism from the controller 60. The at least one button 120 may be a push button, a toggle switch, a touch sensor, etc. according to various embodiments of the present invention.

Additionally, or alternatively, a knob 122 may be operably coupled to the controller 38 through the housing 106. According to one embodiment, the knob 122 may be used to advance and retract the shafts 26, 40 of the endoscope 22 and disposable insert 24. According to other embodiments, the knob 122 may be used to advance and retract auxiliary devices with respect to the shafts 26, 40.

A conduit 124 extend proximally from the hub 36 and through the housing 106 so as to provide passage to the auxiliary devices. For instance, a video camera, light source, or combination thereof may be advanced through the conduit 125 and into the second lumen 86 as described above. Other auxiliary devices may be utilized in a similar way and should not be limited to those specifically described here.

Figure 10:
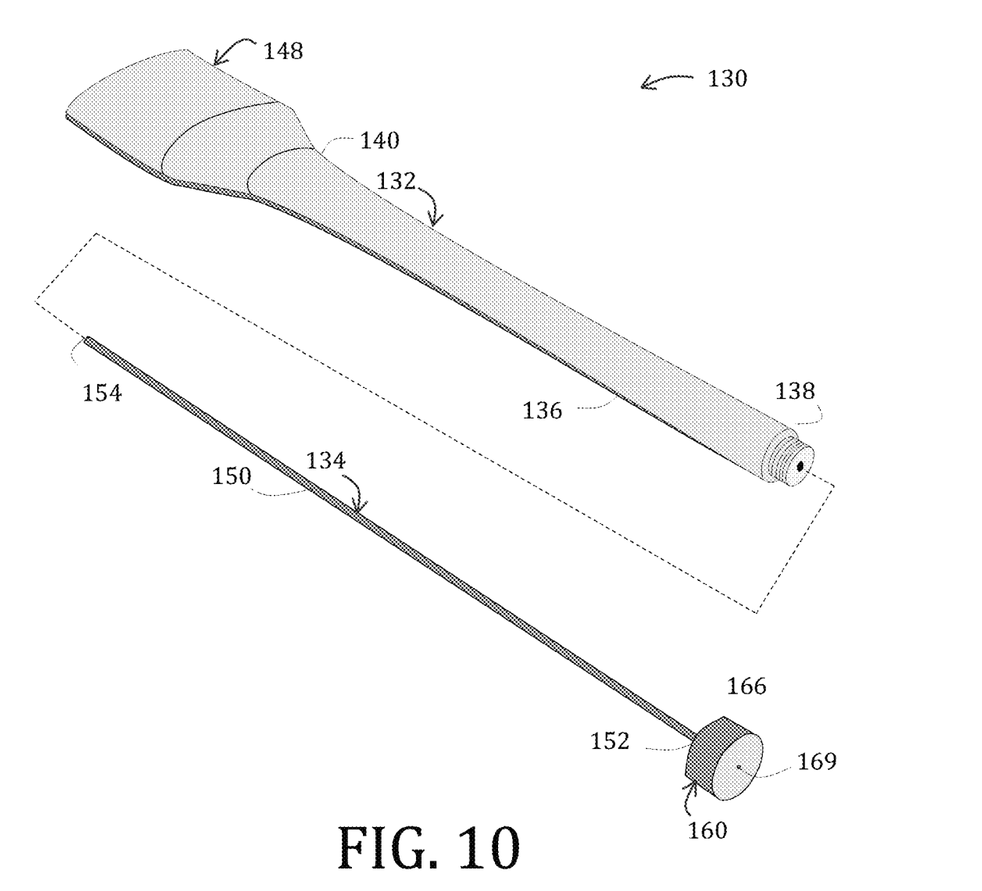
FIG. 10 is an exploded, perspective view of an endoscopic system comprising an endoscope and a disposable insert according to another embodiment of the present invention.
Figure 11A:
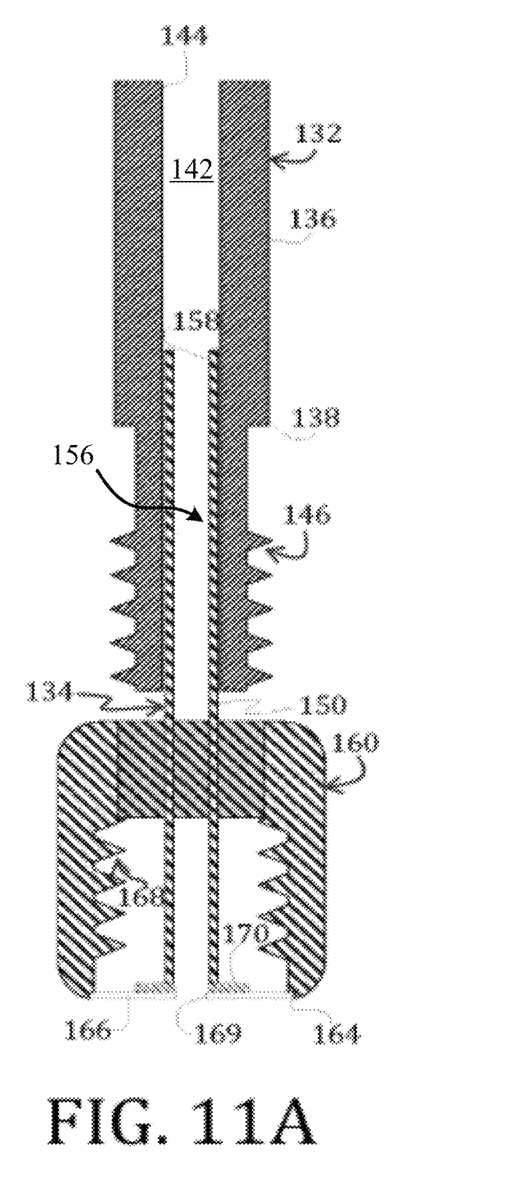
FIGS. 11A and 11B are lengthwise, cross-sectional views of the endoscope and disposable insert of FIG. 10, disassembled and assembled, respectively.
Figure 11B:
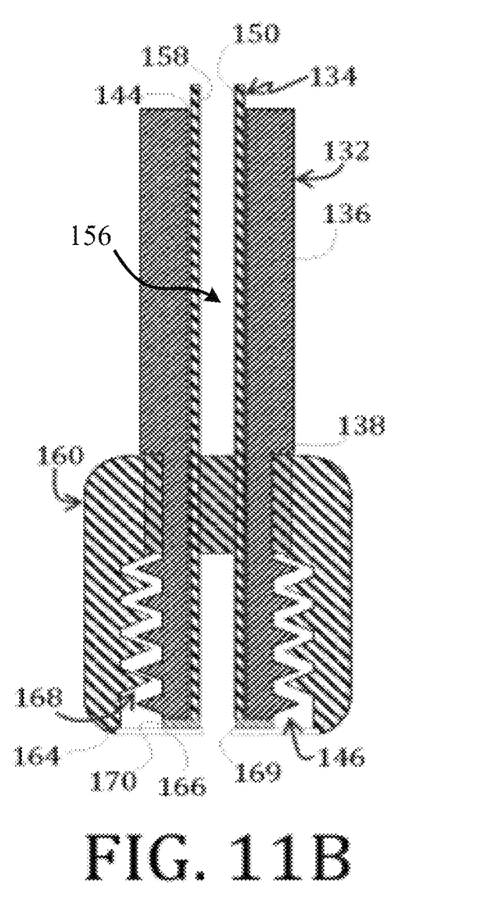

With reference now to FIGS. 10-11B, an endoscopic system 130 in accordance with another embodiment of the present invention and having an endoscope 132 and a disposable insert 134 is shown. The endoscope 132 includes a flexible shaft 136 having a distal end 138, a proximal end 140, and a lumen 142 extending therebetween defined by an inner wall 144. The flexible shaft 134 may be configured and constructed in a manner similar to what was described above with respect to FIG. 1 or in accordance with a manner that is known by those of ordinary skill in the art having the benefit of the disclosure herein. However, unlike the embodiment illustrated in FIG. 1, a threaded portion 146 extends distally from the distal end 138 of the flexible shaft 136. As shown, an outer diameter of the threaded portion 146 is less than an outer diameter of the flexible shaft 134.

The endoscope 132 further comprises a hub 148 operably coupled to the proximal end 140 of the flexible shaft 136. The hub 148 may be configured and constructed in a manner similar to what was described above with respect to FIG. 1 or in accordance with a manner that is known by those of ordinary skill in the art having the benefit of the disclosure herein.

The disposable insert 134 of the endoscopic system 130 includes a flexible shaft 150 having a distal end 152, a proximal end 154, and a lumen 156 extending therebetween defined by an inner wall 158. The disposable insert 134 may be configured and constructed in a manner similar to what was described above with respect to FIG. 1 or in accordance with a manner that is known by those of ordinary skill in the art having the benefit of the disclosure herein.

The distal end 152 of the disposable insert 134 further comprises a cap 160 operably coupled thereto and configured to operably secure the distal end 152 of the disposable insert 134 relative to the distal end 138 of the endoscope 132. The cap 160 further includes a lumen 162 that may be coaxial and coextensive with the lumen 156 of the disposable insert 134. The cap 160 may be configured and constructed in a manner similar to what was described above with respect to FIG. 1 or in accordance with a manner that is known by those of ordinary skill in the art having the benefit of the disclosure herein.

The cap 160 may be substantially cylindrical in cross-section and have a length that is shorter than a length of either flexible shaft 136, 150. The lumen 162 may include a threaded portion 168 configured to receive the threaded portion 146 of the flexible shaft 136 of the endoscope 132.

A distal end 164 of the cap 160 may include an optically transparent window 166 that may be bonded to the cap 160 using adhesives or other connecting materials to form a continuous structure. An orifice 169 within the optically transparent window 166 may be coaxial with the lumen 156 of the flexible shaft 150 and configured to permit fluid communication therethrough.

A gasket 170 may be positioned between the flexible shaft 150 and the transparent window 166 to form a seal between the flexible shaft 150 and the cap 160. The gasket 170 may be configured as an O-ring or other suitable shape, may be constructed from rubber or other suitable material that would not present a risk for tissue reaction or risk of allergy. The relative arrangement of the cap 160, the flexible shaft 136, and the gasket 170 may be secured by way of adhesives or other bonding-like materials.

According to some embodiments, a diameter of the gasket 170 may be such that it extends to engage the threaded portion 146 of the flexible shaft 136 of the endoscope 132. In this way, a fluidic seal may be further established between the endoscope 132 and the disposable insert 134.

In use, the flexible shaft 136 of the endoscope 132 may be advanced into the cap 160 of the disposable insert and then rotated to threadably engage the threaded portion 168 within the lumen of the cap. The engagement forms a fluid-tight seal that limits, or at least restricts, biocontamination to the lumen of the disposable insert 134. After the procedure is complete, the disposable insert 134 may be discarded while the endoscope 132 undergoes sterilization. Because biohazardous materials, including biofilm, are restricted to the disposable insert 134, sterilization procedures are more efficient.

Figure 12:
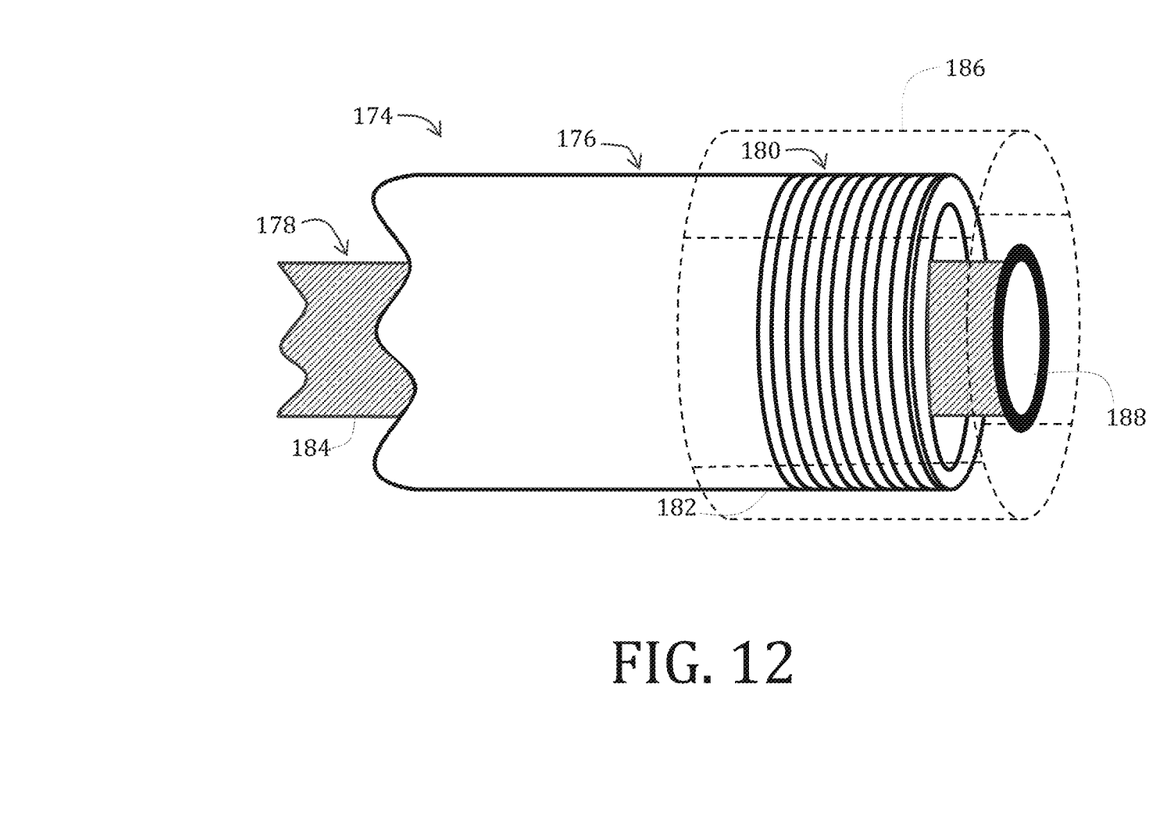
FIG. 12 is a side elevational view of an endoscopic system according to another embodiment of the present invention, with the disposable insert shown in phantom.

With reference now to FIG. 12, the distal end of an endoscopic system 174 according to another embodiment of the present invention is shown and includes an endoscope 176 and a flexible insert 178. The endoscope 176, as shown, may be similar to the endoscope 132 of FIG. 10 having a threaded portion 180 at its distal end 182. The disposable insert 178 includes a flexible shaft 184 and a cap 186 (shown in phantom) positioned on the distal end 188 thereof. The cap 186 may be constructed from a transparent material, such as acrylic, glass, poly(methyl methacrylate) (PMMA), polyimide, plastic material, sapphire, polycarbonates, polymers, zinc-selenide, etc. The cap 186 and the shaft 184 of the disposable insert 178 may be coupled together in a manner similar to the embodiment shown in FIG. 11A, even though the gasket 170 (FIG. 11A) is now shown in FIG. 12.

While not specifically illustrate, yet another embodiment of the present invention may include a disposable insert similar to FIG. 12 having only a portion of a cap being constructed with the transparent material while a remaining portion of the cap may be constructed from a non-transparent material.

Figure 13A:
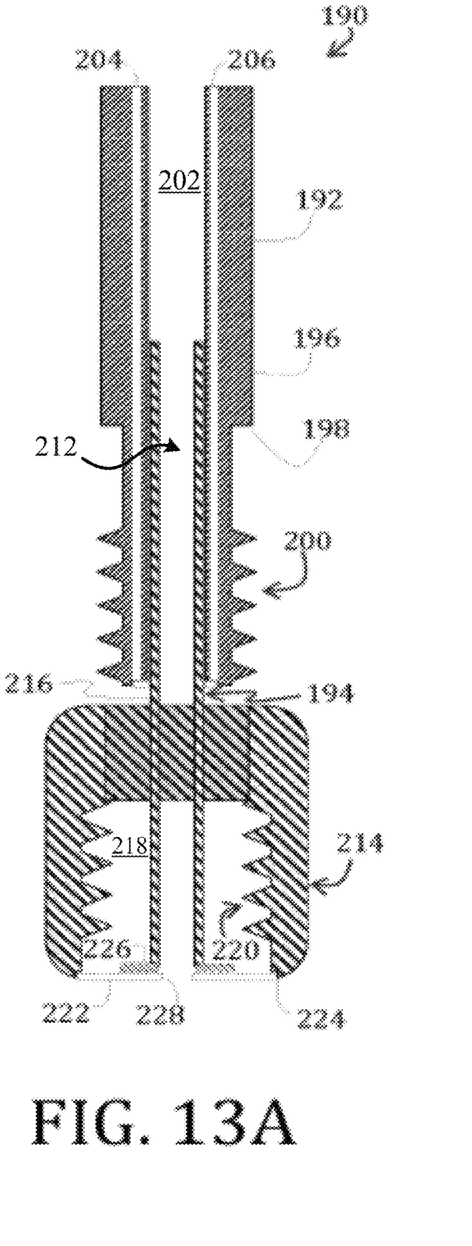
FIGS. 13A and 13B are lengthwise, cross-sectional views of an endoscopic system according to yet another embodiment of the present invention, disassembled and assembled, respectively.
Figure 13B:
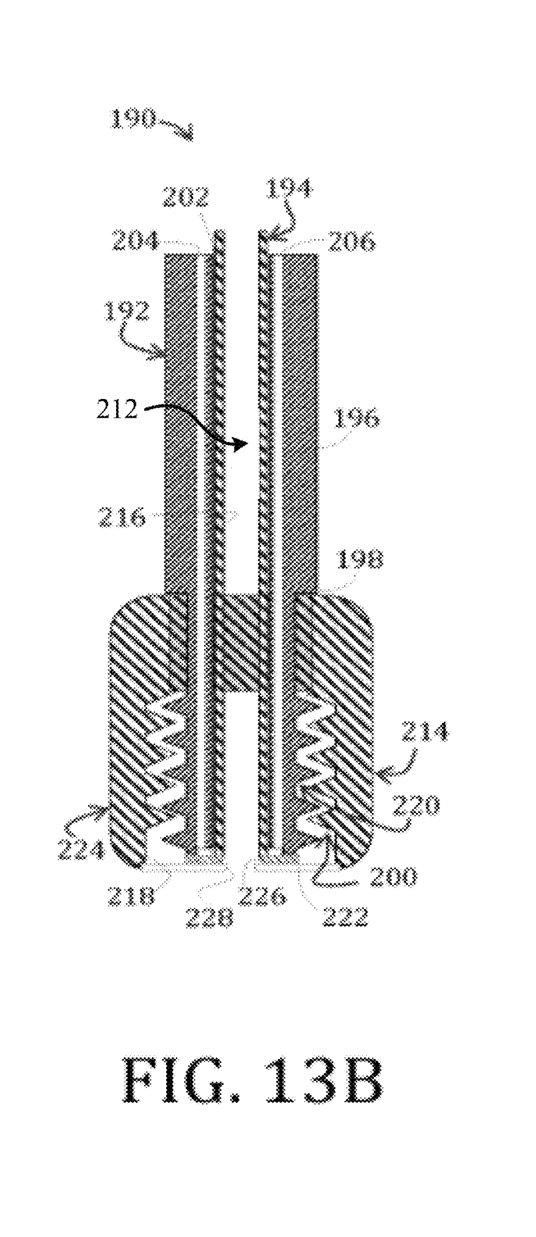

FIGS. 13A and 13B illustrate an endoscopic system 190 according to still another embodiment of the present invention includes an endoscope 192 and a disposable insert 194. The endoscope 192 has a flexible shaft 196, a distal end 198 thereof including a threaded portion 200. As illustrated, three lumen 202, 204, 206 extend the length of the flexible shaft 196. The first lumen 202 is centrally disposed with the second and third lumens 204, 206 laterally offset from the first lumen 202. An optically transparent window 208 is positioned at a distal end 210 of the threaded portion 200 to fluidically seal the second and third lumens 204, 206. In this way, auxiliary devices (not shown) may be utilized through the second and third lumens 204, 206 with reduced risk of biocontamination.

The disposable insert 194 includes a shaft 212 having a cap 214 on a distal end 216 thereof. A lumen 218 extends through the cap 214 and includes a threaded portion 220 that is configured to receive the treaded portion 200 of the shaft 196 of the endoscope 192. An optically transparent window 222 is secured to a distal end 224 of the cap 214 and the flexible shaft 212 of the disposable insert 194 by way of a gasket 226. An orifice 228 in the optically transparent window 222 permits fluid communication therethrough.

The particular arrangement of FIGS. 13A and 13B facilitates the use of auxiliary devices with minimized risk of biocontamination. For instance, illumination from a light source (not shown) in the second lumen 204 may transmit through both the optically transparent window 208 of the endoscope 192 and the optically transparent window 222 of the cap 214 so as to illuminate a surgical site.

Figure 14A:
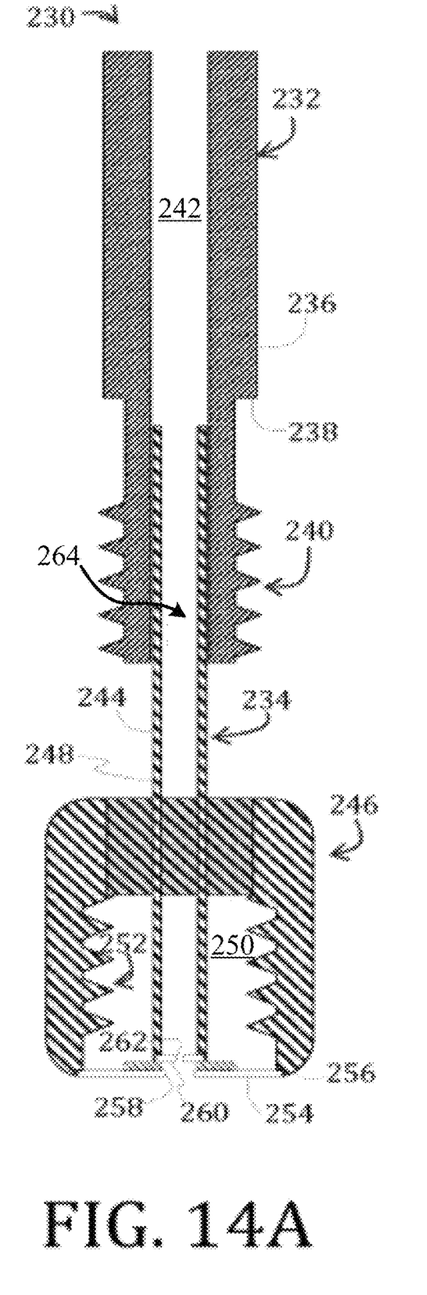
FIGS. 14A and 14B are lengthwise, cross-sectional views of an endoscopic system according to yet another embodiment of the present invention, disassembled and assembled, respectively.
Figure 14B:
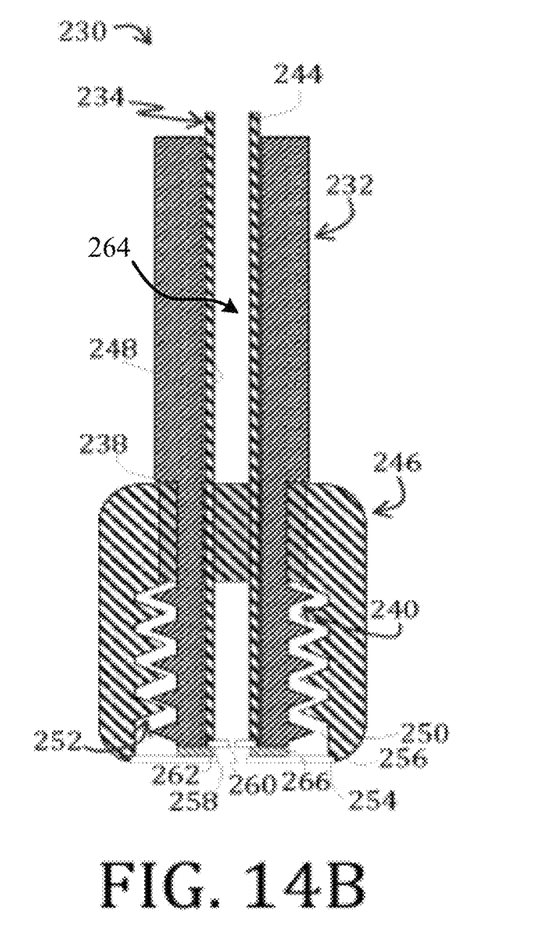

FIGS. 14A and 14B illustrate an endoscopic system 230 according to yet another embodiment of the present invention includes an endoscope 232 and a disposable insert 234. The endoscope 232 has a flexible shaft 236, a distal end 238 thereof including a threaded portion 240, and a lumen 242 extending the length of the flexible shaft 236.

The disposable insert 234 includes a shaft 244 having a cap 246 on a distal end 248 thereof. A lumen 250 extends through the cap 246 and includes a threaded portion 252 that is configured to receive the treaded portion 240 of the shaft 236 of the endoscope 232. The cap 246 further comprises an optically transparent window 254 on a distal end 256 thereof having an orifice 258 therein for provided fluid communication through the lumen 250 of the cap 246.

An optically transparent window 260 is secured the shaft 244 and includes an orifice 262 to provide fluid communication with a lumen 264 of the shaft 244. The optically transparent window 260 and, thereby, the shaft 244, may be coupled to the optically transparent window 254 of the cap 246 by way of a gasket 266.

Embodiments of the disclosed invention, its various features and the advantageous details thereof, are explained more fully with reference to the non-limiting embodiments that are illustrated in the accompanying drawings and detailed in the following description. Descriptions of well-known components and processing techniques are omitted to not unnecessarily obscure what is being disclosed. Examples may be provided and when so provided are intended merely to facilitate an understanding of the ways in which the invention may be practiced and to further enable those of skill in the art to practice its various embodiments. Accordingly, examples should not be construed as limiting the scope of what is disclosed and otherwise claimed.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Those skilled in the art will recognize that the embodiments herein can be practiced with modification within the spirit and scope of the appended claims.

What is claimed is:

1. A disposable insert for an endoscope, the disposable insert comprising:
a flexible shaft having a shaft distal end, a shaft proximal end, and a shaft lumen extending therebetween, the flexible shaft configured to be received by and within a lumen of the endoscope; and
a cap operably coupled to the shaft distal end of the flexible shaft, the cap comprising a recess, formed with a medial wall and an outer wall, wherein the medial wall and the outer wall are located within the cap, and the medial wall is configured to receive and threadably engage with threads located on a distal end of the endoscope such that the threads located on the distal end of the endoscope are within the recess in the cap to secure the flexible shaft to the endoscope and form a fluid-tight seal therewith, the cap having a cap lumen extending therethrough that is coaxial to the shaft lumen of the flexible shaft.

2. The disposable insert of claim 1, wherein the shaft proximal end of the flexible shaft is configured to be operably coupled to a hub of the endoscope.

3. The disposable insert of claim 2, wherein the shaft proximal end of the flexible shaft is configured to be operably coupled to a controller within the hub of the endoscope.

4. The disposable insert of claim 3, wherein the controller is configured to control at least one operation of the endoscope through the disposable insert, the at least one operation selected from suction, irrigation, lighting, imaging, mechanical manipulation, or electrical manipulation.

5. The disposable insert of claim 4, wherein the controller is removable from the hub and is disposable.

6. The disposable insert of claim 1, wherein the cap is at least partially constructed from an optically transparent material.

7. The disposable insert of claim 6, wherein the optically transparent material comprises one or more of an acrylic, glass, poly (methyl methacrylate) (PMMA), a polyimide, plastic material, sapphire, polycarbonates, polymers, or zinc-selenide.

8. The disposable insert of claim 6, wherein an entirety of the cap is constructed from the optically transparent material.

9. The disposable insert of claim 1, wherein the flexible shaft is constructed from silicon, plastic, or other hypoallergenic material.

10. The disposable insert of claim 1, wherein the cap further comprises a seal configured to form the fluid-tight seal when the flexible shaft threadably engages the distal end of the endoscope.

11. An endoscopic system comprising:
an endoscope comprising:
- a first flexible shaft having a first proximal end, a first distal end, and a first lumen extending therebetween, the first distal end comprising threads;
- a hub coupled to the first proximal end of the first flexible shaft; and
- a controller within the hub operably coupled to the first lumen and configured to control at least one operation, the at least one operation selected from suction, irrigation, lighting, imaging, mechanical manipulation, or electrical manipulation; and a disposable insert comprising:
- a second flexible shaft having a second proximal end, a second distal end, and a second lumen extending therebetween, the second flexible shaft of the disposable insert being configured to be received by and within the first flexible shaft of the endoscope; and
- a cap operably coupled to the second distal end of the second flexible shaft and configured to secure the second flexible shaft to the first distal end of the first flexible shaft via a recess, formed with a medial wall and an outer wall, wherein the medial wall is configured to receive and threadably engage with the threads located on the first distal end of the endoscope to form a fluid-tight seal therewith, the cap having a third lumen extending therethrough that is coaxial to the second lumen of the second flexible shaft and configured to receive the first flexible shaft, wherein the second proximal end of the second flexible shaft is operably coupled to the controller such that the at least one operation is performed through the second lumen of the second flexible shaft.

12. The endoscopic system of claim 11, wherein the controller is removable from the hub and is disposable.

13. The endoscopic system of claim 11, wherein the cap is at least partially constructed from an optically transparent material.

14. The endoscopic system of claim 13, wherein the optically transparent material comprises one or more of an acrylic, glass, poly (methyl methacrylate) (PMMA), a polyimide, a plastic material, sapphire, polycarbonates, polymers, or zinc-selenide.

15. The endoscopic system of claim 13, wherein an entirety of the cap is constructed from the optically transparent material.

16. The endoscopic system of claim 13, wherein the second flexible shaft is constructed from silicon, plastic, or other hypoallergenic material.

17. The endoscopic system of claim 11, wherein the cap further comprises a seal configured to form the fluid-tight seal when the first and second flexible shafts threadably engage.

18. The endoscopic system of claim 13, wherein the endoscope further comprises lighting fibers, camera fibers, steering components, or combinations thereof.

19. The disposable insert of claim 1, wherein:
the medial wall comprises threading to engage an inner wall of the distal end of the endoscope.

20. The endoscopic system of claim 11, wherein:
the medial wall comprising threading to engage the threads located on an inner wall of the first distal end of the endoscope.

21. The disposable insert of claim 1, wherein the cap further comprises one or more optically transparent windows, wherein the one or more optically transparent windows align with at least one lumen located in an exterior wall of the endoscope.

22. The disposable insert of claim 1, wherein the cap further comprises one or more optically transparent windows that are secured to the cap using one or more intervening components.

23. The disposable insert of claim 22, wherein the one or more intervening components comprise one or more of a distal lip or proximal lip.

* * * * *